(12) United States Patent
Adolphi et al.

(10) Patent No.: US 9,074,976 B2
(45) Date of Patent: Jul. 7, 2015

(54) VISCOSITY MEASURING METHOD

(75) Inventors: Natalie L. Adolphi, Albuquerque, NM (US); Edward R. Flynn, Albuquerque, NM (US); Howard Bryant, Albuquerque, NM (US); Kimberly Butler, Rockville, MD (US)

(73) Assignees: STC.UNM, Albuquerque, NM (US); Senior Scientific, LLC, Albuquerque, NM (US)

( * ) Notice: Subject to any disclaimer, the term of this patent is extended or adjusted under 35 U.S.C. 154(b) by 238 days.

(21) Appl. No.: 13/385,671

(22) Filed: Feb. 29, 2012

(65) Prior Publication Data

US 2012/0234080 A1    Sep. 20, 2012

Related U.S. Application Data

(60) Provisional application No. 61/464,210, filed on Mar. 1, 2011.

(51) Int. Cl.
*G01N 11/12* (2006.01)
*B82Y 15/00* (2011.01)
*G01N 11/00* (2006.01)

(52) U.S. Cl.
CPC .............. *G01N 11/12* (2013.01); *B82Y 15/00* (2013.01); *G01N 2011/0086* (2013.01)

(58) Field of Classification Search
CPC .............. G01N 2011/00; G01N 2011/0026; G01N 2011/004; G01N 2011/0086; G01N 2011/006; G01N 11/00; G01N 11/02; G01N 11/04; G01N 11/08; G01N 11/10; G01N 11/12; G01N 11/14; G01N 11/16; G01N 24/081; G01N 24/00; B82Y 25/00; B82Y 35/00; A61B 5/1486

USPC ............ 73/54.01, 54.02, 54.24, 54.27, 54.41, 73/64.56; 600/573, 347, 365, 368, 369, 600/370, 465, 466, 486, 504, 309; 977/960, 977/904, 956
See application file for complete search history.

(56) References Cited

U.S. PATENT DOCUMENTS

| | | | |
|---|---|---|---|
| 2002/0124634 A1* | 9/2002 | Litton | 73/54.25 |
| 2006/0010963 A1* | 1/2006 | Bach et al. | 73/54.01 |

(Continued)

FOREIGN PATENT DOCUMENTS

WO    WO 2009026164 A1 *   2/2009    ............. G01N 24/08

OTHER PUBLICATIONS

Iddo M. Gescheit, A Proposed Method for Thermal Specific Bioimaging and Therapy Technique for Diagnosis and Treatment of Malignant Tumors by Using Magnetic Nanoparticles, Apr. 9, 2008, Advances in Optical Technologies, Article ID 275080.*

(Continued)

*Primary Examiner* — Hezron E Williams
*Assistant Examiner* — Marrit Eyassu

(57) ABSTRACT

A method for measuring the average viscosity of a test fluid uses calibrated magnetic nanoparticles, with certain chosen hydrodynamic diameters and actual lateral dimensions (e.g. diameters), that are mixed into a small volume of the test fluid and a single magnetic relaxation curve measurement to provide data for viscosity determination. The distribution of hydrodynamic particle sizes of an ensemble of magnetic nanoparticles that are magnetically blocked at room temperature can be determined. Modifications of the method can be used to determine the distribution of viscosities in a complex fluid at the sub-microscopic level providing a novel type of viscosity measurement.

10 Claims, 2 Drawing Sheets

(56) References Cited

U.S. PATENT DOCUMENTS

| | | | |
|---|---|---|---|
| 2006/0213283 A1* | 9/2006 | Morris et al. | 73/861.12 |
| 2008/0038769 A1* | 2/2008 | Bernardi et al. | 435/29 |
| 2008/0220411 A1* | 9/2008 | McNaughton et al. | 435/5 |
| 2009/0085557 A1* | 4/2009 | Krozer et al. | 324/201 |
| 2010/0109653 A1* | 5/2010 | Nieuwenhuis et al. | 324/204 |
| 2013/0149539 A1* | 6/2013 | Krishnan et al. | 428/407 |
| 2013/0323165 A1* | 12/2013 | Campbell et al. | 424/1.21 |

OTHER PUBLICATIONS

Zaner, K.S. et al., Viscoelasticity of F-Actin Measured with Magnetic Microparticles, The Journal of Cell Biology, vol. 109, Nov. 1989, pp. 2233-2243.

Breedveld, V. et al., Microrheology as a tool for high-throughput screening, Journal of Materials Science 38, 2003, pp. 4461-4470.

Weihs, D. et al., Bio-Microrheology: A Frontier in Microrheology, Biophysical Journal, vol. 91, Dec. 2006, pp. 4296-4305.

* cited by examiner

VISCOSITY MEASURING METHOD

RELATED APPLICATION

This application claims benefits and priority of U.S. provisional application Ser. No. 61/464,210 filed Mar. 1, 2011, the entire disclosure of which is incorporated herein by reference.

CONTRACTUAL ORIGIN OF THE INVENTION

This invention was made under grants R44 CA096154, R44 AI066765, R44 CA105742, and R44 CA123785, awarded by the National Institutes of Health. The government has certain rights in the invention.

FIELD OF THE INVENTION

This invention relates to a method of measuring viscosity of a fluid and, more particularly, to a method of measuring viscosity by magnetic relaxometry using magnetic nanoparticles dispersed in a test fluid.

BACKGROUND OF THE INVENTION

The measurement of viscosity of a fluid is important in many industries and applications where fluid properties need to be monitored and controlled.

In biology and medicine, viscosity measurements are important for understanding a variety of complex biological fluids, such as engineered polymers, the interior of living cells, and blood. These measurements aid in the fundamental understanding of biological processes and the ability to monitor and control human disease. For example, blood viscosity is an important parameter in monitoring diabetic patients and patients receiving blood transfusions. Many industrial products including food products, household and industrial chemicals, pharmaceutical products, and cosmetics are complex fluids, and the ability to monitor viscosity therefore has many potential applications in industrial or pharmaceutical R&D, process monitoring, and quality control.

Relaxometry measurements have been used to evaluate cytoplasmic motions, rheology, and structure using magnetic nanoparticle probes. For example, Valberg and Feldman, The Journal Of Cell Biology, volume 101, pp. 130-140, 1985, as well as Valberg and Albertini, Biophysical Journal, Volume 52, pp. 551-561 1987, describe testing of hamster lung cells with ingested ferromagnetic nanoparticles by first subjecting the cells to a brief magnetizing field pulse having an initial orientation followed by measurement of the decay of the remanent magnetic field (relaxation) of the cells in a weaker, re-oriented magnetic field that imparts torque to the nanoparticles. The re-orientation of the magnetic fields allows the driven particle rotation to be evaluated and intracellular apparent viscosity determined from the rate of particle rotation. Spontaneous (Brownian) relaxation of the nanoparticles (i.e. without the weaker, re-oriented) magnetic field is also described.

SUMMARY OF THE INVENTION

The present invention provides in one illustrative embodiment a method for measuring the average viscosity of a test fluid using magnetic nanoparticles introduced in the test fluid wherein magnetic nanoparticles have certain features selected to enable a magnetic relaxometry measurement to yield data from which average viscosity can be readily determined using, for example, simple algebraic equations.

In an illustrative embodiment of the present invention, the magnetic nanoparticles are chosen to have a hydrodynamic diameter that yields a magnetic relaxation time within a certain time range, such as, for example, 10-2000 ms. Composite particles typically are used each comprising multiple magnetic nanoparticles held together by a non-magnetic coating (matrix) wherein the hydrodynamic diameter is adjusted for the intended measurement by the thickness or amount of a coating (matrix). Preferably, the magnetic nanoparticles have an actual major lateral dimension (e.g. diameter) defining an individual nanoparticle volume (domain volume) that is large enough to substantially reduce or eliminate Neel relaxation effects (negligible Neel relaxation effect) on the relaxometry measurement.

In practicing this illustrative embodiment of the present invention, the method for measuring the average viscosity of a test fluid involves measuring magnetic relaxation of the magnetic nanoparticles in the test fluid after termination of the magnetic field pulse, determining a decay time constant of the magnetic relaxation of the nanoparticles in the test fluid, determining a calibrated decay time constant of the relaxation of like nanoparticles in a calibration fluid, and determining viscosity of the test fluid using the time constants and the known viscosity of the calibration fluid. The viscosity determination can be corrected for Neel relaxation effects in another illustrative embodiment. The magnetic nanoparticles can be calibrated in a calibration fluid such as, for example, water, in the event the viscosity of blood or other water-based fluid is to be determined.

Practice of this embodiment of the present invention is advantageous in that the hydrodynamic diameter of the magnetic nanoparticles does not need to be precisely known; only the viscosity of the calibration fluid needs to be known. Moreover, the calibration of the magnetic nanoparticles in the calibration fluid only needs to be performed once for a large batch of nanoparticles that can then be used to probe hundreds of test solutions.

The present invention provides in another illustrative embodiment a method for determining the distribution of hydrodynamic diameters of an ensemble of magnetic nanoparticles introduced in a substantially homogenous "control" fluid using magnetic relaxometry wherein the magnetic relaxometry data provide a B vs. t decay curve which is the sum of many single-exponential decays with different decay time constants, from which a distribution of decay time constants can be determined. Mathematical analysis such as, inverse Laplace transformation, of the decay time constants can determine a distribution (i.e. histogram) of decay time values that are proportional to the distribution of the hydrodynamic sizes (diameters). The amplitude of the distribution at a particular decay time constant (corresponding to a particular size) indicates the number of magnetic particles in the ensemble with that particular size. This embodiment is a potential alternative to DLS (dynamic light scattering) for measuring the hydrodynamic size distribution of particles.

The present invention provides in still a further embodiment a method for determining distribution of viscosity values of a test fluid by relaxometry measurement by determining a hydrodynamic diameter distribution of magnetic nanoparticles introduced in a control fluid according to the previous paragraph, introducing the magnetic nanoparticles in the test fluid, subjecting the test fluid to a magnetic field pulse, and measuring a plurality of relaxation curves of the nanoparticles in the test fluid, determining a distribution of decay time constants from the relaxation curves. Mathematical analysis such as, inverse Laplace transformation, of the decay time constants can determine a distribution (histogram) of decay time values that are proportional to the distribution of viscosities of the test fluid. The amplitude of the distribution at a particular decay time constant (corresponding to a particular viscosity) indicates the volume of the test fluid that has that particular value of viscosity. This embodiment is useful for determining the distribution of viscosities in a complex fluid at the sub-microscopic level, thereby providing a novel type of viscosity measurement. For example, a gelatin contains a random distribution of proteins in water, and the viscosity will be higher in portions of the sample where the proteins are more densely packed and lower in microscopic regions containing mostly free water.

Other advantages and features of the present invention will become apparent from the following drawings taken with the detailed description of the invention.

DESCRIPTION OF THE INVENTION

Figure 1:
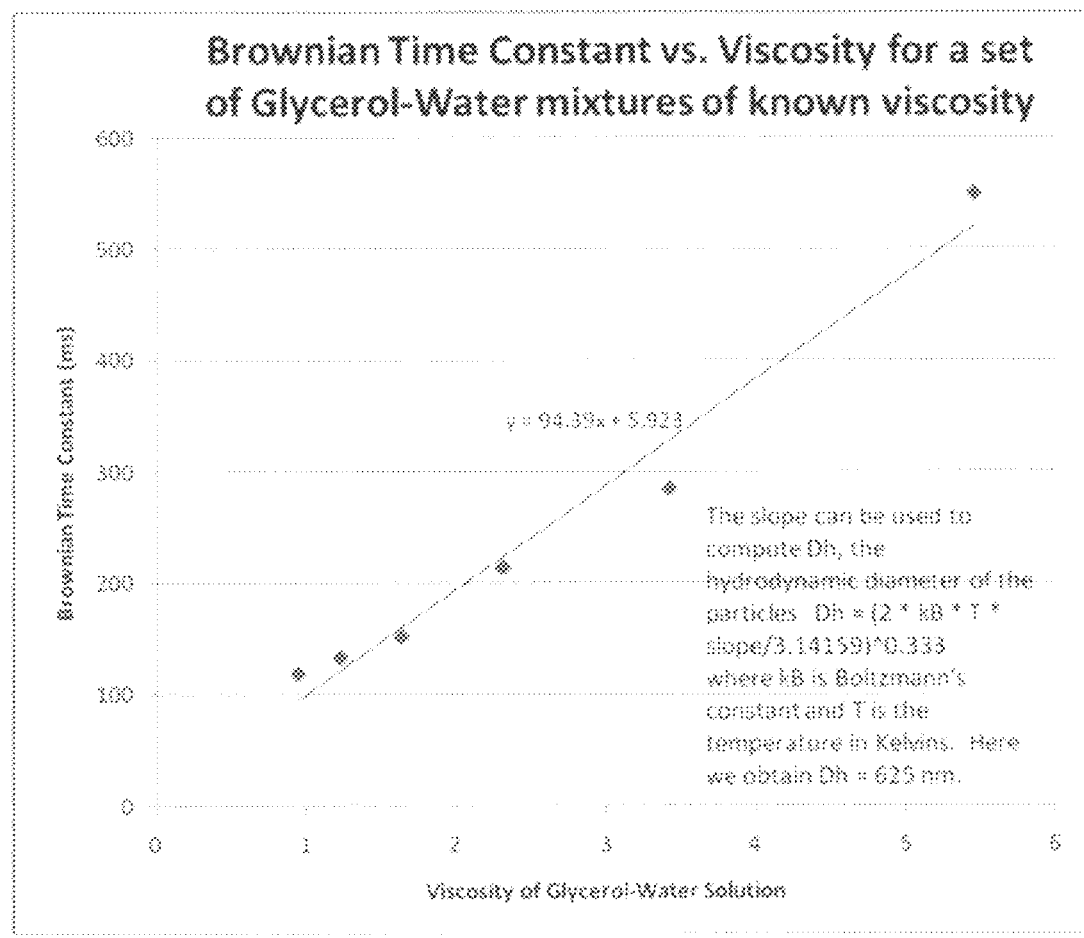
FIG. 1 is a plot of Brownian time constants versus viscosity of glycerol-water solutions.

The present invention provides in an illustrative embodiment a method for measuring average viscosity of a test fluid using magnetic nanoparticle having certain selected features chosen to enable a single magnetic relaxometry measurement to yield data from which average viscosity can be readily determined quickly (e.g. in less than one minute) using, for example, simple algebraic equations. Calibration of the magnetic nanoparticles in a calibration fluid only needs to be performed once for a large batch of nanoparticles that can then be used to probe hundreds of test fluids. For purposes of illustration and not limitation, when the test fluid is blood or other water-based fluid, the calibration fluid typically is water such as de-ionized water, and the nanoparticles would be suspended in an aqueous solution miscible in both the calibration fluid and the test fluid. When the test fluid is oil or a lipid, the calibration fluid can be an organic solvent, such as benzene, and the nanoparticles would be suspended in an organic solvent miscible in both the calibration fluid and the test fluid. The present invention is especially useful for measuring the average viscosity of biological fluids, such as blood, plasma, saliva, and mucus, although it is not so limited and can be practiced to measure average viscosity of any other test fluids of interest.

As will become apparent below, analysis of the relaxometry data in this illustrative embodiment can be conducted using only two simple algebraic equations without precisely knowing in advance the hydrodynamic size of the magnetic nanoparticles. Only the viscosity of the calibration solution needs to be known (at the temperature at which the measurement is performed) and is readily available in the literature for simple fluids, such as water.

In practice of the present invention the magnetic nanoparticles are provided to have hydrodynamic diameter and actual dimensional features that are tailored to enable use of a single magnetic relaoxmetry measurement to quickly probe anticipated viscosities of the test fluid preferably without adverse Neel relaxation effects on the measurement. For example, for testing a blood sample, relatively monodispersed magnetic nanoparticles are employed having a hydrodynamic diameter that will yield a magnetic relaxation time that falls in the anticipated 10-2000 ms range so that blood viscosities can be quickly probed. For purposes of illustration and not limitation, a hydrodynamic diameter of at least about 500 nm, such as from 500 nm to about 1000 nm would be appropriate for probing viscosities in the 0.001-0.005 Pa-s range, the range in which blood generally falls.

Commercially available magnetic nanoparticles can be used in practice of certain embodiments of the invention. Such magnetic nanoparticles typically are provided in the form of composite particles that each comprises multiple magnetic nanoparticles (particle clusters or aggregates) held together by a non-magnetic coating (matrix) wherein the hydrodynamic diameter is adjusted for the intended measurement by the thickness or amount of a coating (matrix). Typically, the major lateral dimension (e.g. actual diameters) of the nanoparticles in a cluster will vary as a consequence of commercial nanoparticle manufacturing methods. The collective or aggregate particle diameters and the coating (matrix) thickness holding the cores together as an aggregate or cluster collectively provide the overall hydrodynamic diameter desired for quick relaxometry measurement. The magnetic nanoparticles each can comprise a ferromagnetic, ferrimagnetic or other suitable magnetically susceptible material such as including, but not limited to, gamma hematite ($Fe_2O_3$), magnetite ($Fe_3O_4$), maghetite, or others, while the coating can be a non-magnetic, chemically inert substance, such as a polymer, starch, or silica, that does not dissolve or melt in the test fluid. Nanoparticle size can be in the range of about 5 to about 50 nm diameter or more such as for magnetite and others for purposes of illustration.

In practicing a preferred embodiment of the invention, the composite particles should comprise magnetic nanopartcles that have an actual lateral dimension (e.g. diameter) defining an individual nanoparticle volume (domain volume) that is large enough to substantially reduce or eliminate Neel relaxation effects (negligible Neel relaxation effect) on the relaxometry measurement. For purposes of illustration and not limitation, preferred composite particles can include multiple magnetite nanoparticles uniformly distributed in the non-magnetic coating (matrix) out of contact with one another with each nanoparticle having a diameter that is about 40 nm or more in order to substantially reduce or eliminate adverse Neel relaxation effects on the relaxometry measurement, while the non-magnetic coating (matrix holding the cores together) can have a thickness to provide the particle hydrodynamic diameter set forth above for quickly probing an anticipated range of blood viscosities. Moreover, for further illustration, if available, the invention envisions alternately using magnetic nanoparticles each comprising a single magnetite nanoparticle (i.e. not clusters) that has a diameter that is about 40 nm or more in order to substantially reduce or eliminate adverse Neel relaxation effects on the relaxometry measurement and a thick non-magnetic coating on each nanoparticle to provide the desired hydrodynamic diameter.

Exemplary Viscosity Determination:

In practice of an illustrative embodiment of the invention, the measurement of average viscosity of biological water-based fluids (or other water-based fluid of interest) involves the following steps:

Step 1. Providing magnetic nanoparticles having features tailored to enable use of a single relaxometry measurement to probe an anticipated range of viscosities of the test fluid. For testing a blood sample, one such feature is to use relatively monodispersed magnetic nanoparticles having a hydrodynamic diameter that will yield a magnetic relaxation time that falls in the desired 10-2000 ms range for blood. For example, for blood, magnetic nanoparticles with a hydrodynamic diameter of about 500 nm to about 1000 nm would be appropriate for probing viscosities in the 0.001-0.005 Pa-s range, the range in which blood generally falls.

Step 2. Adding a small volume of these magnetic nanoparticles already disposed at high concentration in a nanoparticle-containing fluid to a much larger volume of the test fluid such that the addition of the nanoparticles does not appreciably alter the viscosity of the test fluid. For purposes of illustration and not limitation, when a blood sample is to be tested, the small volume of magnetic nanoparticles is introduced in de-ionized water, which is miscible in blood, and then this small volume is added to the much larger-volume blood sample. For purposes of further illustration and not limitation, the small volume of the nanoparticle-containing fluid can be only 2 microliters while the large-volume blood sample can be 500 microliters to this end.

Step 3a. Measuring the magnetic relaxation curve (B vs. t) of previously magnetized nanoparticles in the test fluid in the absence of a magnetic field. For example, the relaxometry measurement involves the application of a pulsed DC magnetic field (e.g. 0.005 Tesla for 0.75 s) followed by recording of the remnant magnetic field B as a function of t (time) in zero applied magnetic field (i.e. zero applied field) using any type of magnetic field or flux sensor with sufficient sensitivity, e.g. SQUID, atomic magnetometer, fluxgate magnetometer, etc. Then, fitting the B vs. t curve with a single exponential decay function (i.e., B=B0*exp(−t/tauS)), where B0 is the initial magnetic field value, to obtain the exponential relaxation time constant (decay constant) characterizing relaxation of the magnetic nanoparticles in the test fluid (i.e., relaxation time constant=tauS) in the absence of a magnetic field.

Step 3b. Using a similar method as Step 3a, measuring the relaxation curve (B vs. t) of the same volume of nanoparticle-containing fluid in a volume of de-ionized water (as a calibration fluid) equal to the volume of the test sample. (De-ionized water at a known temperature has a well-known viscosity, which will be used to calibrate the measurement of the unknown viscosity.) Then, fitting the curve with a single exponential decay function (i.e., B=B0*exp(−t/tauW)) to obtain the exponential relaxation time constant (decay constant) characterizing relaxation of the nanoparticles in the de-ionized water (i.e., calibrated relaxation time constant=tauW) in the absence of a magnetic field.

Step 3c. Optionally also measuring the relaxation curve (B vs. t) using a similar measurement method of a similar quantity of the same nanoparticles immobilized to prevent Brownian rotation. To immobilize the particles, the nanoparticle-containing fluid may be prepared in a variety of ways (e.g. dried on a cotton swab or mixed into a mannitol solution and freeze-dried, etc.) If a relaxation curve is observed from the immobilized nanoparticles, it will likely not fit a single exponential curve over all times. However, the average Neel relaxation time (time between flips of the particle magnetization direction) can be estimated by a number of computational methods. The simplest of which is to fit the curve with a single exponential decay function (i.e., B=B0*exp(−t/tauN) over only the early portion of the decay (perhaps 50-300 ms, where 0 ms is the moment when the magnetic field pulse is switched off) to obtain an exponential time constant characterizing the Neel relaxation of the immobilized nanoparticles (i.e., Neel relaxation time constant=tauN).

All of the above measurements are performed at the same well-controlled temperature, such as 72 degrees F. (i.e. room temperature) or any other testing temperature for purposes of illustration and not limitation.

Step 3d. Data analysis: The Brownian time constant is known to be directly proportional to the viscosity. Also, the Brownian time constant is related to the time constants measured in Steps 3a, 3b, 3c in the following way:

$$tauSb = 1/(1/tauS - 1/tauN) \qquad \text{Eq. 1}$$

$$tauWb = 1/(1/tauW - 1/tauN) \qquad \text{Eq. 2}$$

where tauSb is the Brownian time constant for the test fluid of interest, and tauWb is the Brownian time constant for the de-ionized water calibration fluid.

Because the viscosity, Eta, is linearly proportional to the Brownian time constant, the following formula is obtained:

$$EtaS/EtaW = tauSb/tauWb \qquad \text{Eq. 3}$$

Therefore:

$$EtaS = EtaW*(tauSb/tauWb). \qquad \text{Eq. 4}$$

In other words, the viscosity of the test fluid of interest (EtaS) is given by multiplying the known viscosity of water by the ratio of the Brownian time constants of the nanoparticles in the test fluid and the water (calibration fluid). Once the Neel time constant (tauN) and the Brownian time constant in water (tauWb) are determined for a given batch of nanoparticles, aliquots of that batch of nanoparticles can be used to measure the viscosity of a large number of test fluids. In other words, to calibrate the nanoparticles, measurement Steps 3b and 3c described above need to be performed only once to determine tauN and tauW (and then tauWb is calculated from Eq. 2). After the magnetic nanoparticles are calibrated (in the water calibration fluid), measurement Step 3a can be performed on a large number of different test fluids to measure their viscosities, and the viscosity of each test fluid can then be computed using Eqs. 1 and 4.

After the calibration is complete and the tauN and tauW values are entered in a spread sheet or computer program, the time required to determine the viscosity of a new test fluid (of unknown viscosity) will be approximately one (1) minute for purposes of illustration only.

This one (1) minute estimate includes sample preparation (mixing in the nanoparticles in the test fluid), measuring the relaxation time, and analyzing the result. Using automated sample loading and data analysis, the time to determine the viscosity of a single sample could be reduced to a couple of seconds.

In practice of the illustrative embodiment described above, a correction factor could be developed to accommodate the effect of the addition of the nanoparticles to the test fluid. This correction factor could easily be incorporated into the viscosity measurement.

EXAMPLE 1

Viscosity Determination

An illustrative method embodying steps 1, 2, and 3 above for a calibration fluid was conducted using a set of water/glycerol mixtures of known composition (and therefore known viscosity), as shown in FIG. 1. For the data below and in FIG. 1, the water-glycerol mixtures were prepared by a formula to give a particular set of viscosity values (plotted against the x-axis below).

Figure 2:
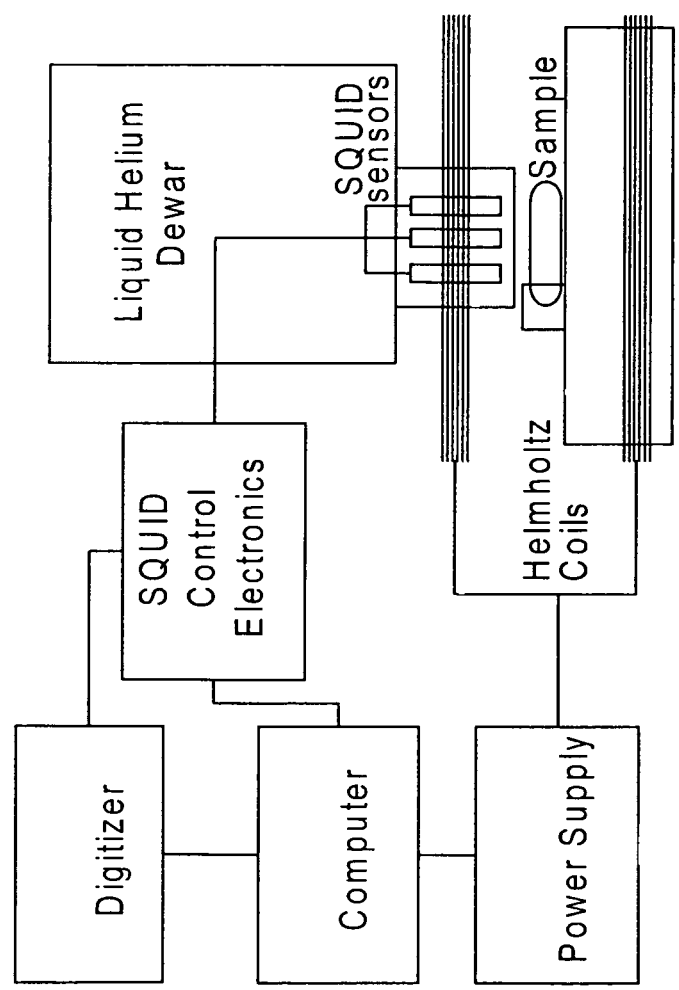
FIG. 2 is a schematic view of the test equipment employed to generate the data of Example 1

In this Example, the Brownian time constant (decay constant) was measured using the equipment schematically shown in FIG. 2 using a SQUID sensor to measure the relaxation time constant of commercially-available FluidMAG CMX magnetic composite nanoparticles of nominal 200 nm overall hydrodynamic diameter (per vendor information) in the glycerol-water mixtures, and correcting for the Neel relaxation contribution by obtaining the Neel time constant from nanoparticles dried on a cotton swab. tauN=approximately 91 ms. The FluidMAG CMX magnetic composite nanoparticles are commercially available from a vendor, Chemicell, GmbH, Berlin. Each FluidMAG CMX composite particle comprised aggregates or clumps of multiple magnetite particles having individual random actual lateral dimensions (e.g. diameters) of approximately 5-25 nm held or stuck together by a starch coating or matrix to provide the nominal overall hydrodynamic diameter of 200 nm per the vendor information. The Brownian time constant was measured using a pulsed DC magnetic field (field strength of 0.005 T and pulse time duration of 0.75 s) followed by recording B (magnetic field) as a function of t (time) in zero applied field using a commercially available SQUID device (a BTi 2004 seven-channel low-temperature SQUID array made by 4D-Neuroimaging; San Diego, Calif., USA, originally designed for magnetoencephalography). In the sensor system, second order gradiometers with a baseline of 4.0 cm are used to reject background magnetic fields due to distant sources, allowing the measurements to be performed without magnetic shielding. Due to RF interference, the sensitivity of the sensors is currently limited to $\sim 10^{-12}$ T/$\sqrt{Hz}$. The seven gradiometer coils are located at the bottom of the liquid He dewar, arranged with six in a circle of 2.0 cm radius and one at the center. For this measurement, the sample was located at a distance z$\approx$3 cm below the bottom of the center gradiometer. The sample was uniformly magnetized (parallel to the center gradiometer axis) using a pair of 49 cm diameter, 100 turn Helmholtz coils powered by a 5 kW current-regulated power supply (Sorenson SGA 80/63). The current through the magnetizing coils was monitored by a Hall Effect transducer to assure constant magnetic fields. The decaying magnetization was sampled at a rate of 8 kHz (beginning 40 ms after switching off the magnetizing pulse), digitized using a National Instruments PXI8336 16-channel digitizer, and acquired using software written in LabWindows™/CVI (National Instruments, Austin, Tex., USA). Acquired data was decimated by a factor of 8 (down to 1 kHz) to improve signal-to-noise. The measurement protocol was: a) apply a 4.9 mT field for 0.75 s, b) acquire data for 2.215 s, c) repeat for a total of 10 acquisitions and average the results. The early part of the B vs. t decay curve was then fit with a decaying exponential function to obtain the decay time constant. The data shown in FIG. 1 approximately fit a straight line with y-intercept close to zero, indicating that the equation:

$$tauB=PI*Dh^3*Eta/(2*kB*T)$$

is reasonably-well satisfied. (PI=3.14159, Dh is hydrodynamic diameter in meters, Eta is viscosity in units of Pa-s, kB is Boltzmann's constant in J/K, T is temperature in Kelvins, and tauB is the time constant in s) Independent confirmation of the viscosities of the mixtures can determine if the "standard curve" shown in FIG. 1 is entirely accurate. Accuracy of the curve can be improved by using the more preferred magnetic nanoparticles described herein. The temperature could also be varied for a water sample to vary Eta in a more controlled and reproducible way. The standard curve shown in FIG. 1 can now be used to determine the viscosity of an unknown test fluid (like blood), by obtaining tauB of the blood sample and then reading off the corresponding Eta value from the graph, FIG. 1, or alternately, by using the linear fit equation and computing the value of Eta for the unknown sample as described above in Equation 4.

EXAMPLE 2

Preferred Relaxometry Test

In a preferred embodiment of the present invention, the magnetic nanoparticles are chosen in a manner to substantially reduce or eliminate the Neel relaxation effects on the relaxometry measurement. As a result, there will be no correction for the Neel relaxation component, as all viscosity probe nanoparticles will have a Neel relaxation time constant much longer than the measurement timescale (i.e. their magnetic relaxation will be "blocked"). In other words, it is preferred to use nearly monodisperse particles that are all "blocked" to eliminate Neel relaxation at the measurement temperature. Therefore these nanoparticles would only exhibit detectable relaxation that is caused by Brownian rotational motion, which depends on hydrodymic diameter and viscosity. In this preferred embodiment, the measured relaxation times tauS and tauW would be equal to the Brownian time constants without any need for a Neel correction factor. That is, for "blocked" particles, the Neel relaxation time is effectively infinite, so that the rate correction (1/tauN), required for obtaining the Brownian time constants in Equations 1 and 2 is effectively zero.

To this end, each "blocked" magnetic nanoparticle, whether present with other nanoparticles in a composite particle or present as single, individually coated nanoparticles, will have an actual lateral dimension (e.g. diameter) defining an individual particle volume (domain volume) that is large enough to substantially reduce or eliminate Neel relaxation effects (negligible Neel relaxation effect) on the relaxometry measurement. For purposes of illustration and not limitation, in this preferred embodiment, monodisperse magnetite magnetic nanoparticles each having an actual lateral dimension (e.g. diameter) of 40 nm diameter or more can be used in conjunction with a substantial coating (e.g. polystyrene or other polymer coating) as a matrix to hold them together in a cluster or as an individual nanoparticle coating to bring the hydrodynamic diameter up to the required level for the fluid to be tested and would be a preferred magnetic nanoparticle design for the relaxomery measurement.

EXAMPLE 3

Hydrodynamic Particle Size Determination

The present invention envisions in another illustrative embodiment a method for determining the distribution of hydrodynamic sizes of an ensemble of magnetic nanoparticles that are introduced in a substantially homogenous "control" fluid, such as the de-ionized water calibration fluid described above, if the magnetic nanoparticles are all magnetically "blocked" at the measurement temperature as also described above.

Using steps similar those embodied in Step 3b above, the magnetic relaxometry measurement would simultaneously provide a plurality of B vs. t decay curves wherein the number of component curves would depend on the hydrodynamic particle size distribution. From a single measured B vs. t curve (the sum of the component curves), a plurality of exponential time constants (decay constants) can be determined. Obtainment of the distribution of hydrodynamic sizes involves inverting the relaxation curves using an inverse Laplace transformation, such as CONTIN or another similar algorithm, to obtain the distribution of relaxation time values [by operating on a single function (a single B vs. t curve) that is a sum of single exponential decays (sum of Bi*exp(−t/taui) where i denotes particles i and the sum runs over i=1 to N where N is the number of different particles]. The Laplace transform operates on this function to return the distribution of time constants (i.e. the histogram of taui values). In a homogeneous Newtonian fluid (such as de-ionized water), the distribution of relaxation times would be directly proportional to the distribution of hydrodynamic particle sizes (because viscosity, Eta, would be a constant) such that the inverse Laplace transformation would yield a histogram corresponding to the distribution of hydrodynamic particle sizes.

EXAMPLE 4

Distribution of Viscosities in Complex Fluid

Once the distribution of hydrodynamic diameters is determined from the water calibration fluid using "blocked" nanoparticles (as described above in the "Hydrodynamic particle size determination"), then this information could be used to determine if the test fluid (the fluid whose viscosity is to be measured) exhibits a single value of viscosity or a distribution of viscosity values. The local nature of the magnetic nanoparticles enables characterization of the distribution of viscosity values present in fluids with spatially inhomogeneous viscosity (i.e. different viscosities at different points in the fluid, because the fluid itself is inhomogeneous on the scale of the nanoparticle size).

For example, in blood, magnetic nanoparticles with a hydrodynamic diameter of 500 nm (i.e. 0.5 micron) would be smaller than many of the constituents of blood (i.e. various types of blood cells, which are 5-15 microns in diameter). In other words, when considering the spatial dimensions of the nanoparticle probe, blood is inhomogeneous, because water molecules are smaller than the probe but blood cells are larger than the probe. A nanoparticle that is wedged between two blood cells may exhibit slow relaxation (high apparent viscosity), while a nanoparticle that is floating about more freely in the plasma might exhibit faster relaxation (lower apparent viscosity).

An illustrative method involves determining a hydrodynamic size distribution of magnetic nanoparticles dispersed in a control fluid as described above in the "Hydrodynamic particle size determination", introducing the magnetic nanoparticles in the test fluid, subjecting the test fluid to a magnetic field pulse, and measuring a plurality of relaxation curves of the nanoparticles in the test fluid whose number would depend on the different local viscosities of the test fluid, and determining a distribution of decay time constants from the relaxation curves. Mathematical analysis such as, inverse Laplace transformation, of the decay time constants can be used to determine a distribution of decay time values that are proportional to the convolution of the distribution (histogram) of viscosities of the test fluid with the distribution of hydrodynamic diameters. Since the distribution of hydrodynamic particle sizes is known, deconvolution yields the distribution of viscosities. If the distribution of hydrodynamic sizes is extremely narrow (i.e. the particles are essentially monodisperse with respect to hydrodynamic diameter), then the distribution of decay time values measured from the test fluid would yield the distribution of viscosities of the test fluid directly (without deconvolution). The latter situation (probe particles with uniform hydrodynamic size) would be preferable. This embodiment is useful for determining the distribution of viscosities in a complex fluid at the sub-microscopic level, thereby providing a novel type of viscosity measurement.

EXAMPLE 5

Measurement of Viscosity of a Homogeneous Test Fluid Using Nanoparticles of Monodisperse Hydrodynamic Size if Neel Relaxation is not Eliminated There are two design criteria for the preferred magnetic nanoparticles: 1) negligible Neel relaxation, and 2) uniform hydrodynamic size. In the case that condition 1 is not met (i.e. the nanoparticles exhibit Neel relaxation on the timescale of the measurement) but condition 2 is satisfied, an alternative method of correcting for Neel relaxation can be used. i.e. an alternative to the method in example 1.

First, measure the relaxation of magnetic nanoparticles of uniform hydrodynamic size, immobilized (e.g. by freeze-drying) to determine the Neel relaxation curve, B vs. t. If the particles have a distribution of Neel relaxation times, the relaxation curve will be given by:

$$B(t)=\Sigma_{i=1\ to\ N}[Bi*\exp(-t/tauNi)] \quad \text{Eq. A}$$

This is a sum of single-exponential decay terms, where the index i denotes an individual nanoparticle, there are N nanoparticles in the ensemble, and the Neel relaxation time constant of the ith nanoparticle is denoted tauNi. Typically, for polydisperse cores, the function B(t) can be well-approximated by the function:

$$B(t)=C*\ln(1+tauc/t) \quad \text{Eq. B}$$

where C is a constant, ln is the natural logarithm, and tauc is the "characteristic" relaxation time of the ensemble (reference Chantrell et al., J. Magn. Magn. Mater. 38 (1983) 133). Thus, the relaxation data from the immobilized particles can be fit by this function to obtain the parameters C and tauc. This function will be used to correct for the Neel relaxation below.

Now introduce some nanoparticles from the same batch into a calibration fluid and measure B vs. t. In this case, the relaxation will be caused by Brownian rotation and Neel relaxation, and rearranging equation 1, the relaxation time constant for a given nanoparticle will be given by $$1/tauSi=1/tauSb+1/tauNi \quad \text{Eq. C}$$

and the observed relaxation for the ensemble, in the calibration fluid (assume water, W), will be given by $$B(t) = \sum_{i=1\ to\ N} [Bi*\exp(-t/tauWi)] \quad \text{Eq. D}$$
$$= \sum_{i=1\ to\ N} [Bi*\exp(-t*(1/tauWb+1/tauNi))]$$
$$= \sum_{i=1\ to\ N} [Bi*\exp(-t/tauWb)*\exp(-t/tauNi)]$$

Now because all of the particles have the same Brownian time constant (because they are monodisperse in hydrodynamic size and the medium is homogeneous), the factor exp(−t/tauWb) is the same for all particles and can be moved outside of the summation.

$$B(t)=\exp(-t/tauWb)*\Sigma_{i=1\ to\ N}[Bi*\exp(-t/tauNi)] \quad \text{Eq. E}$$

In this case, the second term (i.e. the summation) is the same as Eq. A, which can be replaced by Eq. B, as explained above, resulting in $$B(t)=\exp(-t/tauWb)*C*\ln(1+tauc/t), \quad \text{Eq. F}$$

and C and tauc are already known from fitting the Neel relaxation of the immobilized particles above. Therefore, $$\exp(-t/tauWb)=B(t)/(C*\ln(1+tauc/t))=B'(t) \quad \text{Eq. G}$$

In other words, dividing the data at each time point t (i.e. B(t)) by the function given in Eq. B (evaluated at each corresponding t value) will yield a new function, B'(t), which is a single-exponential decay with time constant tauWb. The function B'(t) can now be fitted with a single-exponential decay to obtain tauWb, and the hydrodynamic size Dh computed using the equation:

$$tauWb=PI*Dh\char`\^3*EtaW/(2*kB*T)$$

Once Dh is known for the batch of nanoparticles in use, nanoparticles from the same batch can be added to a test fluid. B vs. t can be measured for the test fluid, and the following equation is used to compute B'(t)

$$\exp(-t/tauSb)=B(t)/(C*\ln(1+tauc/t))=B'(t)$$

This equation is the same as Eq. G except that tauSb is the Brownian time constant of the sample (i.e. test) fluid in this case. Fitting B'(t) with a single-exponential then yields tauSb, and Eq. 4 (above) can again be used to compute EtaS (the viscosity of the test fluid), using the known value of EtaW and the values of tauWb and tauSb that were just obtained by analyzing the B'(t) data.

In view of the above examples, it should be apparent that practice of the present invention is advantageous in that average viscosity can be measured using calibrated magnetic nanoparticles and a single magnetic relaxometry measurement that can be quickly conducted (e.g. in less than 1 minute) without knowing the hydrodynamic size of the magnetic nanoparticles precisely. Moreover, the nanoparticle calibration only needs to be performed once for a large batch of nanoparticles that can then be used to probe hundreds of test solutions. And, the analysis of the data is based on two simple algebraic equations discussed above. The hydrodynamic size of the nanoparticles does not need to be known precisely in advance for this technique. Only the viscosity of the calibration solution needs to be known. In addition, practice of the present can enable measurement of the distribution of hydrodynamic sizes of an ensemble of nanoparticles that are magnetically "blocked" at the measurement temperature. The present invention also can provide a new measurement method of the distribution of viscosities in a complex fluid at the sub-microscopic level using this technique.

Although the present invention has been described with respect to certain illustrative embodiments, those skilled in the art will appreciate that changes and modifications can be made thereto within the spirit of the invention as set forth in the appended claims.

We claim:

1. A method of measuring the viscosity of a test fluid using calibrated magnetic particles having a hydrodynamic size distribution, comprising
    1) a calibration step involving calibrating the magnetic particles having said hydrodynamic size distribution by introducing them into a calibration fluid of known viscosity, subjecting the calibration fluid to a magnetic field pulse to rotate the magnetic particles, then measuring Brownian rotational magnetic relaxation of the pulse-induced magnetization of the magnetic particles in the calibration fluid after termination of the magnetic field pulse, and determining a single decay time constant of the magnetization of the magnetic particles in the calibration fluid, and
    2) a test fluid measuring step involving introducing into the test fluid magnetic particles of the same type having the same hydrodynamic size distribution as used in the calibration step, subjecting the test fluid to a magnetic field pulse to rotate the magnetic particles without altering the hydrodynamic size distribution used in the calibration step, then measuring Brownian rotational magnetic relaxation of the pulse-induced magnetization of the magnetic particles themselves in the test fluid after termination of the magnetic field pulse, determining a single decay time constant of the magnetization of the magnetic particles in the test fluid, and determining viscosity of the test fluid from a ratio of the decay time constant determined from the test fluid and the decay time constant determined from the calibration fluid of the known viscosity wherein the viscosity of the test fluid varies linearly with the single decay time constant measured from the test fluid.

2. The method of claim 1 including introducing in the test fluid composite particles each comprising multiple nanoparticles held together by a non-magnetic coating or matrix to achieve a selected range of hydrodynamic diameters.

3. The method of claim 1 wherein each magnetic particle has an actual lateral dimension selected large enough to reduce or eliminate Neel relaxation effects on the magnetic relaxation measurement.

4. The method of claim 1 wherein the magnetic particles are introduced in a first fluid and then the particle-containing first fluid is mixed into the test fluid wherein the first fluid and the test fluid are miscible.

5. The method of claim 1 wherein the Brownian magnetic relaxation of the particles themselves is detected in a magnetic field that is no greater than an ambient magnetic field present in a room where the measurement is made.

6. The method of claim 1 wherein the viscosity, EtaS, of the test fluid is determined using the equation:

$$EtaS = EtaW \times tauSb/tauWb,$$

wherein EtaW is the viscosity of the calibration fluid, tauSb is the Brownian time constant of the particles in the test fluid, and tauWb is a calibrated Brownian time constant of the particles in the calibration fluid.

7. The method of claim 6 wherein the viscosity is determined by determining the Brownian time constant of the particles in the test fluid and obtaining a viscosity value of the test fluid from a correlation plot of calibrated Brownian time constants in a series of calibration fluids versus viscosity of the calibration fluids.

8. The method of claim 1 including adjusting the determination of viscosity by a Neel relaxation correction of the particles.

9. The method of claim 1 including calibrating the magnetic particles in water as the calibration fluid when the test fluid is blood or other water-based fluid.

10. The method of claim 1 wherein the particles comprise a ferromagnetic or ferrimagnetic material.

* * * * *